(12) United States Patent
Hodges et al.

(10) Patent No.: US 7,901,459 B2
(45) Date of Patent: Mar. 8, 2011

(54) SPLIT SPINAL DEVICE AND METHOD

(75) Inventors: Scott D. Hodges, Ooltewah, TN (US); Steven C. Humphreys, Chattanooga, TN (US); Marc M. Peterman, Memphis, TN (US); Randall Allard, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1220 days.

(21) Appl. No.: 11/031,780

(22) Filed: Jan. 7, 2005

(65) Prior Publication Data

US 2005/0154465 A1 Jul. 14, 2005

Related U.S. Application Data

(60) Provisional application No. 60/534,960, filed on Jan. 9, 2004.

(51) Int. Cl.
*A61F 2/44* (2006.01)

(52) U.S. Cl. .................... 623/17.14; 623/17.15

(58) Field of Classification Search .... 623/17.11–17.16, 623/16.11
See application file for complete search history.

(56) References Cited

U.S. PATENT DOCUMENTS

| | | |
|---|---|---|
| 4,349,921 A | 9/1982 | Kuntz |
| 4,697,582 A | 10/1987 | Williams |
| 4,702,930 A | 10/1987 | Heide et al. |
| 4,759,769 A | 7/1988 | Hedman et al. |
| 4,932,975 A | 6/1990 | Main et al. |
| 5,092,866 A | 3/1992 | Breard et al. |
| 5,258,031 A | 11/1993 | Salib et al. |
| 5,282,863 A | 2/1994 | Burton |
| 5,387,213 A | 2/1995 | Breard et al. |
| 5,401,269 A | 3/1995 | Buttner-Janz et al. |
| 5,415,661 A | 5/1995 | Holmes |
| 5,507,816 A | 4/1996 | Bullivant |
| 5,554,194 A * | 9/1996 | Sanders ............ 623/17.17 |
| 5,556,431 A | 9/1996 | Buttner-Janz |
| 5,562,660 A | 10/1996 | Grob |
| 5,562,737 A | 10/1996 | Graf |

(Continued)

FOREIGN PATENT DOCUMENTS

DE 101 35771 A1 2/2003

(Continued)

OTHER PUBLICATIONS

U.S. Appl. No. 11/342,961, filed Jan. 30, 2006, Yu, et al.

(Continued)

*Primary Examiner* — Eduardo C Robert
*Assistant Examiner* — Tara R Carter

(57) ABSTRACT

An artificial spinal joint for creating at least a portion of a coupling between a superior vertebra and an inferior vertebra is disclosed. The artificial spinal joint comprises a first arthroplasty half comprising a first articulating joint replacement component for placement in an intervertebral disc space between the superior and inferior vertebrae, a first posterior joint replacement component, and a first bridge component coupled between the first articulating joint replacement component and the first posterior joint replacement component. The artificial spinal joint further comprises a second arthroplasty half comprising a second articulating joint replacement component for placement in an intervertebral disc space between the superior and inferior vertebrae, a second posterior joint replacement component, and a second bridge component coupled between the second articulating joint replacement component and the second posterior joint replacement component. The first articulating joint replacement component is engaged with the second articulating joint replacement component.

46 Claims, 9 Drawing Sheets

U.S. PATENT DOCUMENTS

| | | | |
|---|---|---|---|
| 5,562,738 | A | 10/1996 | Boyd et al. |
| 5,672,175 | A | 9/1997 | Martin |
| 5,674,296 | A | 10/1997 | Bryan et al. |
| 5,676,701 | A | 10/1997 | Yuan et al. |
| 5,702,450 | A | 12/1997 | Bisserie |
| 5,895,428 | A | 4/1999 | Berry |
| 5,899,941 | A | 5/1999 | Nishijima et al. |
| RE36,221 | E | 6/1999 | Breard et al. |
| 5,961,516 | A | 10/1999 | Graf |
| 6,039,763 | A | 3/2000 | Shelokov |
| RE36,758 | E | 6/2000 | Fitz |
| 6,113,637 | A | 9/2000 | Gill |
| 6,132,464 | A | 10/2000 | Martin |
| 6,146,421 | A | 11/2000 | Gordon et al. |
| 6,156,067 | A | 12/2000 | Bryan et al. |
| 6,179,874 | B1 | 1/2001 | Cauthen |
| 6,179,875 | B1 | 1/2001 | Strempel |
| 6,228,118 | B1 | 5/2001 | Gordon |
| 6,325,827 | B1 | 12/2001 | Lin |
| 6,368,350 | B1 | 4/2002 | Erickson et al. |
| 6,387,130 | B1 * | 5/2002 | Stone et al. ................ 623/17.16 |
| 6,402,750 | B1 | 6/2002 | Atkinson et al. |
| 6,419,703 | B1 | 7/2002 | Fallin et al. |
| 6,517,580 | B1 | 2/2003 | Ramadan et al. |
| 6,527,804 | B1 | 3/2003 | Gauchet et al. |
| 6,540,747 | B1 | 4/2003 | Marino |
| 6,540,785 | B1 | 4/2003 | Gill et al. |
| 6,565,571 | B1 | 5/2003 | Jackowski et al. |
| 6,565,605 | B2 | 5/2003 | Goble et al. |
| 6,572,653 | B1 | 6/2003 | Simonson |
| 6,579,319 | B2 | 6/2003 | Goble et al. |
| 6,582,466 | B1 | 6/2003 | Gauchet |
| 6,582,468 | B1 | 6/2003 | Gauchet |
| 6,610,091 | B1 | 8/2003 | Reiley |
| 6,610,093 | B1 | 8/2003 | Pisharodi |
| 6,669,729 | B2 | 12/2003 | Chin |
| 6,679,915 | B1 | 1/2004 | Cauthen |
| 6,811,567 | B2 | 11/2004 | Reiley |
| 6,908,484 | B2 | 6/2005 | Zubok et al. |
| 6,949,123 | B2 | 9/2005 | Reiley |
| 6,994,727 | B2 | 2/2006 | Khandkar et al. |
| 7,052,515 | B2 | 5/2006 | Simonson |
| 7,083,649 | B2 * | 8/2006 | Zucherman et al. ........ 623/17.11 |
| 7,090,698 | B2 | 8/2006 | Goble et al. |
| 7,291,150 | B2 * | 11/2007 | Graf ............................ 606/86 A |
| 7,311,732 | B2 | 12/2007 | Link et al. |
| 2002/0095154 | A1 | 7/2002 | Atkinson et al. |
| 2002/0123806 | A1 | 9/2002 | Reiley |
| 2002/0133155 | A1 | 9/2002 | Ferree |
| 2002/0151895 | A1 | 10/2002 | Soboleski et al. |
| 2003/0004572 | A1 | 1/2003 | Goble et al. |
| 2003/0009226 | A1 | 1/2003 | Graf |
| 2003/0028250 | A1 * | 2/2003 | Reiley et al. ............... 623/17.11 |
| 2003/0040797 | A1 | 2/2003 | Fallin et al. |
| 2003/0055427 | A1 | 3/2003 | Graf |
| 2003/0139812 | A1 | 7/2003 | Garcia et al. |
| 2003/0139813 | A1 | 7/2003 | Messerli et al. |
| 2003/0191532 | A1 | 10/2003 | Goble et al. |
| 2003/0199981 | A1 | 10/2003 | Ferree |
| 2003/0199982 | A1 | 10/2003 | Bryan |
| 2003/0204259 | A1 | 10/2003 | Goble et al. |
| 2003/0204260 | A1 | 10/2003 | Ferree |
| 2003/0204271 | A1 | 10/2003 | Ferree |
| 2003/0233146 | A1 | 12/2003 | Grinberg et al. |
| 2004/0002761 | A1 | 1/2004 | Rogers et al. |
| 2004/0002762 | A1 | 1/2004 | Hawkins |
| 2004/0006391 | A1 | 1/2004 | Reiley |
| 2004/0024462 | A1 | 2/2004 | Ferree et al. |
| 2004/0030390 | A1 | 2/2004 | Ferree |
| 2004/0030391 | A1 | 2/2004 | Ferree |
| 2004/0049190 | A1 | 3/2004 | Biedermann et al. |
| 2004/0049272 | A1 | 3/2004 | Reiley |
| 2004/0049273 | A1 | 3/2004 | Reiley |
| 2004/0049274 | A1 | 3/2004 | Reiley |
| 2004/0049275 | A1 | 3/2004 | Reiley |
| 2004/0049276 | A1 | 3/2004 | Reiley |
| 2004/0049277 | A1 | 3/2004 | Reiley |
| 2004/0049278 | A1 | 3/2004 | Reiley |
| 2004/0049279 | A1 | 3/2004 | Sevrain |
| 2004/0049281 | A1 | 3/2004 | Reiley |
| 2004/0138749 | A1 | 7/2004 | Zucherman et al. |
| 2004/0181284 | A1 | 9/2004 | Simonson |
| 2004/0181285 | A1 | 9/2004 | Simonson |
| 2005/0143820 | A1 | 6/2005 | Zucherman et al. |
| 2005/0149196 | A1 | 7/2005 | Zucherman et al. |
| 2005/0154461 | A1 | 7/2005 | Peterman et al. |
| 2005/0154462 | A1 | 7/2005 | Zucherman et al. |
| 2005/0154464 | A1 | 7/2005 | Eisermann et al. |
| 2005/0154466 | A1 | 7/2005 | Eisermann et al. |
| 2005/0154467 | A1 | 7/2005 | Peterman et al. |
| 2005/0171608 | A1 | 8/2005 | Peterman et al. |
| 2005/0171609 | A1 | 8/2005 | Humphreys et al. |
| 2005/0171610 | A1 | 8/2005 | Humphreys et al. |
| 2005/0192671 | A1 | 9/2005 | Bao et al. |
| 2005/0234551 | A1 | 10/2005 | Fallin et al. |
| 2005/0234555 | A1 | 10/2005 | Sutton et al. |
| 2005/0240270 | A1 | 10/2005 | Zubok et al. |
| 2005/0256578 | A1 | 11/2005 | Blatt et al. |
| 2005/0261773 | A1 | 11/2005 | Ferree |
| 2005/0277930 | A1 | 12/2005 | Parsons |
| 2005/0277938 | A1 | 12/2005 | Parsons |
| 2005/0283237 | A1 | 12/2005 | Zucherman et al. |
| 2006/0004448 | A1 | 1/2006 | Casey |
| 2006/0009849 | A1 | 1/2006 | Reiley |
| 2006/0036325 | A1 | 2/2006 | Paul et al. |
| 2006/0069438 | A1 | 3/2006 | Zucherman et al. |
| 2006/0069440 | A1 | 3/2006 | Zucherman et al. |
| 2006/0085076 | A1 | 4/2006 | Krishna et al. |
| 2006/0089717 | A1 | 4/2006 | Krishna et al. |
| 2006/0178745 | A1 | 8/2006 | Bartish, Jr. et al. |
| 2008/0015693 | A1 | 1/2008 | LeCouedic |

FOREIGN PATENT DOCUMENTS

| | | |
|---|---|---|
| DE | 20 2004 015198 | 11/2004 |
| EP | 0 677 277 A2 | 10/1995 |
| EP | 1 281 361 A1 | 2/2003 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | WO 00/04851 | 2/2000 |
| WO | WO 01/39678 | 6/2001 |
| WO | WO 01/45576 | 6/2001 |
| WO | WO 02/47586 | 6/2002 |
| WO | WO 03/041618 A2 | 5/2003 |
| WO | WO 03/045262 A2 | 6/2003 |
| WO | WO 03/084449 | 10/2003 |
| WO | WO 03/101350 | 12/2003 |
| WO | WO 2004/034935 | 4/2004 |
| WO | WO 2004/041131 | 5/2004 |
| WO | WO 2004/098465 | 11/2004 |
| WO | WO 2005/112835 | 12/2005 |

OTHER PUBLICATIONS

U.S. Appl. No. 11/343,159, filed Jan. 30, 2006, Braddock, Jr., et al.

U.S. Appl. No. 11/393,488, filed Mar. 30, 2006, Yu, et al.

U.S. Appl. No. 11/494,311, filed Jul. 27, 2006, Yu, et al.

Patent Cooperation Treaty—European Patent Office, "Notification of Transmittal of the International Search Report and the Written Opinion of the Internatinal Searching Authority, or the Declaration," International Application No. PCT/US2005/000648, Jun. 6, 2005, 6 pages.

Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.

Patent Cooperation Treaty—European Patent Office, "Invitation to Pay Additional Fees/Communication Relating to the Results of the Partial International Search," International Application No. PCT/US2005/000586, Jun. 8, 2005, 5 pages.

Patent Cooperation Treaty—European Patent Office, "Notification of Transmittal of the International Search Report and the Written Opinion of the Internatinal Searching Authority, or the Declaration," International Application No. PCT/US2005/000585, Jun. 8, 2005, 6 pages.

Patent Cooperation Treaty—European Patent Office, "Notification of Transmittal of the International Search Report and the Written Opinion of the Internatinal Searching Authority, or the Declaration," International Application No. PCT/US2005/000704, Aug. 23, 2005, 7 pages.

Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.

* cited by examiner

SPLIT SPINAL DEVICE AND METHOD

CROSS-REFERENCE

This application claims priority from U.S. Provisional Patent Application Ser. No. 60/534,960 filed on Jan. 9, 2004, entitled "Posterior Lumbar Arthroplasty." The following applications also claim priority to the above referenced provisional Application and are related to the present application. They are incorporated by reference herein.

- U.S. Utility patent application Ser. No. 11/031,602, filed on Jan. 7, 2005 and entitled "Spinal Arthroplasty Device and Method;"
- U.S. Utility patent application Ser. No. 11/031,603, filed on Jan. 7, 2005 and entitled "Dual Articulating Spinal Device and Method;"
- U.S. Utility patent application Ser. No. 11/031,904, filed on Jan. 7, 2005 and entitled "Interconnected Spinal Device and Method;"
- U.S. Utility patent application Ser. No. 11/031,783, filed on Jan. 7, 2005 and entitled "Mobile Bearing Spinal Device and Method;"
- U.S. Utility patent application Ser. No. 11/031,700, filed on Jan. 7, 2005 and entitled "Support Structure Device and Method;"
- U.S. Utility patent application Ser. No. 11/031,781, filed on Jan. 7, 2005 and entitled "Centrally Articulating Spinal Device and Method;" and
- U.S. Utility patent application Ser. No. 11/031,903, filed on Jan. 7, 2005 and entitled "Posterior Spinal Device and Method."

TECHNICAL FIELD

Embodiments of the invention relate generally to devices and methods for accomplishing spinal surgery, and more particularly in some embodiments, to spinal arthroplasty devices capable of being placed posteriorly into the vertebral disc space. Various implementations of the invention are envisioned, including use in total spine arthroplasty replacing, via a posterior approach, both the disc and facet functions of a natural spinal joint.

BACKGROUND

As is known the art, in the human anatomy, the spine is a generally flexible column that can take tensile and compressive loads, allows bending motion and provides a place of attachment for ribs, muscles and ligaments. Generally, the spine is divided into three sections: the cervical, the thoracic and the lumbar spine. FIG. 1 illustrates schematically the lumbar spinal 1 and the sacrum regions 3 of a healthy, human spinal column. The sections of the spine are made up of individual bones called vertebrae and the vertebrae are separated by intervertebral discs which are situated therebetween.

FIG. 2 illustrates a portion of the right side of a lumbar spinal region with a healthy intervertebral disc 5 disposed between two adjacent vertebrae 7, 9. In any given joint, the top vertebra may be referred to as the superior vertebra and the bottom one as the inferior vertebra. Each vertebra comprises a generally cylindrical body 7a, 9a, which is the primary area of weight bearing, and three bony processes, e.g., 7b, 7c, 7d (two of which are visible in FIG. 2). As shown in FIG. 7A, in which all of the processes are visible, processes 7b, 7c, 7d extend outwardly from vertebrae body 7 at circumferentially spaced locations. The processes, among other functions, provide areas for muscle and ligament attachment. Neighboring vertebrae may move relative to each other via facet components 7e (FIG. 2), which extend from the cylindrical body of the vertebrae and are adapted to slide one over the other during bending to guide movement of the spine. There are two facet joints, each defined by upper and lower facet components, associated with adjacent vertebra. A healthy intervertebral disc is shown in FIG. 3. As shown in FIG. 3, an intervertebral disc has 4 regions: a nucleus pulposus 11, a transition zone 13, an inner annulus fibrosis region 15 and an outer annulus fibrosis 17. Generally, the inner annulus fibrosis region 15 and the outer annulus fibrosis region 17 are made up of layers of a fibrous gristly material firmly attached to the vertebral bodies above and below it. The nucleus pulposus 11 is typically more hydrated in nature.

These intervertebral discs function as shock absorbers and as joints. They are designed to absorb the compressive and tensile loads to which the spinal column may be subjected while at the same time allowing adjacent vertebral bodies to move relative to each other a limited amount, particularly during bending (flexure) of the spine. Thus, the intervertebral discs are under constant muscular and/or gravitational pressure and generally are the first parts of the lumbar spine to show signs of "wear and tear".

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

One surgical procedure for treating these conditions is spinal arthrodesis (i.e., spine fusion), which has been performed both anteriorally and/or posteriorally. The posterior procedures include in-situ fusion, posterior lateral instrumented fusion, transforaminal lumbar interbody fusion ("TLIF") and posterior lumbar interbody fusion ("PLIF"). Solidly fusing a spinal segment to eliminate any motion at that level may alleviate the immediate symptoms, but for some patients maintaining motion may be advantageous. It is also known to surgically replace a degenerative disc or facet joint with an artificial disc or an artificial facet joint, respectively. However, none of the known devices or methods provide the advantages of the embodiments of the present disclosure.

Accordingly, the foregoing shows there is a need for an improved spinal arthroplasty that avoids the drawbacks and disadvantages of the known implants and surgical techniques.

SUMMARY

In one embodiment, an artificial spinal joint for creating at least a portion of a coupling between a superior vertebra and an inferior vertebra is disclosed. The artificial spinal joint comprises a first arthroplasty half comprising a first articulating joint replacement component for placement in an intervertebral disc space between the superior and inferior vertebrae, a first posterior joint replacement component, and a first bridge component coupled between the first articulating joint replacement component and the first posterior joint replacement component. The artificial spinal joint further comprises a second arthroplasty half comprising a second articulating joint replacement component for placement in an intervertebral disc space between the superior and inferior vertebrae, a second posterior joint replacement component, and a second bridge component coupled between the second articulating joint replacement component and the second posterior joint replacement component. The first articulating joint replacement component is engaged with the second articulating joint replacement component.

In another embodiment, a method of implanting an artificial spinal joint comprises creating a first exposure through a patient's back to access an intervertebral space and creating a second exposure through the patient's back to access the intervertebral space. The method further comprises delivering a first articulating assembly portion of the artificial spinal joint to the intervertebral space along a first path through the first exposure and delivering a second articulating assembly portion of the artificial spinal joint to the intervertebral space along a second path through the second exposure. The method further comprises engaging the first and second articulating assembly portions to form a unitized intervertebral joint centered about an anterior-posterior axis defined through the center of the intervertebral disc space.

In another embodiment, a system for creating a coupling between a superior vertebra and an inferior vertebra is disclosed. The system comprises a first anterior articulating assembly for implantation through a first approach into an intervertebral disc space between the superior and inferior vertebrae and a first posterior articulating assembly connected to the first anterior articulating assembly and extending posteriorly of the intervertebral disc space. The first anterior articulating assembly comprises a caudal articulating surface engaged with a rostral articulating surface wherein the engagement of the caudal and rostral articulating surfaces defines a lateral half of a ball and socket type joint. The lateral half of a ball and socket type joint abuts a central anterior-posterior axis through the intervertebral disc space.

The embodiments disclosed may be useful for degenerative changes of the lumbar spine, post-traumatic, discogenic, facet pain or spondylolisthesis, and/or to maintain motion in multiple levels of the lumbar spine.

Additional and alternative features, advantages, uses and embodiments are set forth in or will be apparent from the following description, drawings, and claims.

DESCRIPTION

The drawings illustrate various embodiments of an artificial intervertebral joint for replacing an intervertebral disc or the combination of an intervertebral disc and at least one corresponding facet joint. Various embodiments of the artificial intervertebral joint according to the principles of the disclosure may be used for treating any of the problems that lend themselves to joint replacement including particularly, for example, degenerative changes of the lumbar spine, post-traumatic, discogenic, facet pain or spondylolisthesis and/or to maintain motion in multiple levels of the lumbar spine.

Figure 1:
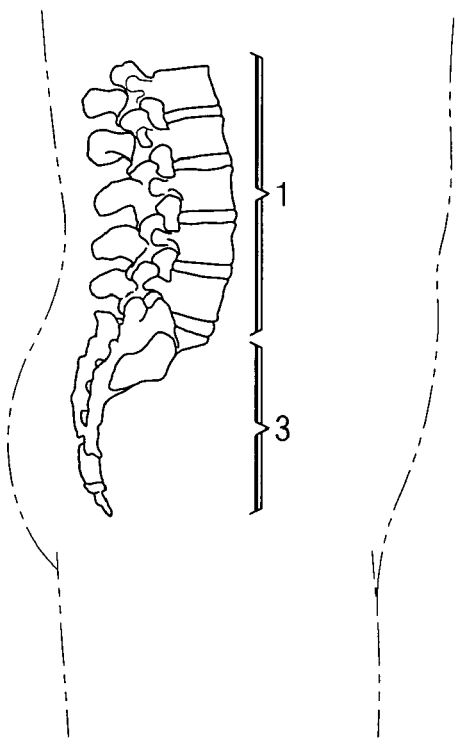
FIG. 1 is a side elevation schematic view of the lumbar spinal and the sacrum regions of a healthy, human spinal column.
Figure 2:
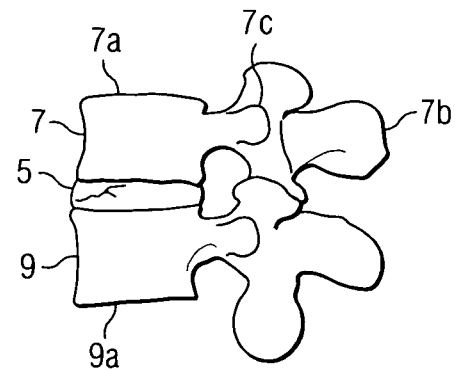
FIG. 2 is a detailed perspective view showing a portion of the right side of the lumbar vertebrae shown in FIG. 1 with a healthy disc disposed between two vertebrae.
Figure 3:
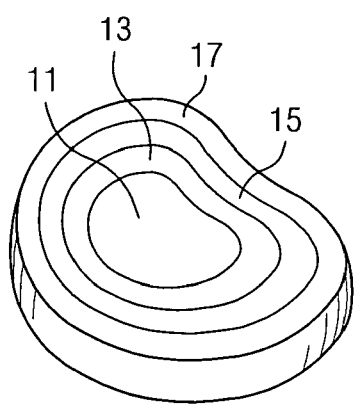
FIG. 3 is a top perspective view of the intervertebral disc shown in FIG. 2 illustrating the major portions of the disc.
Figure 4:
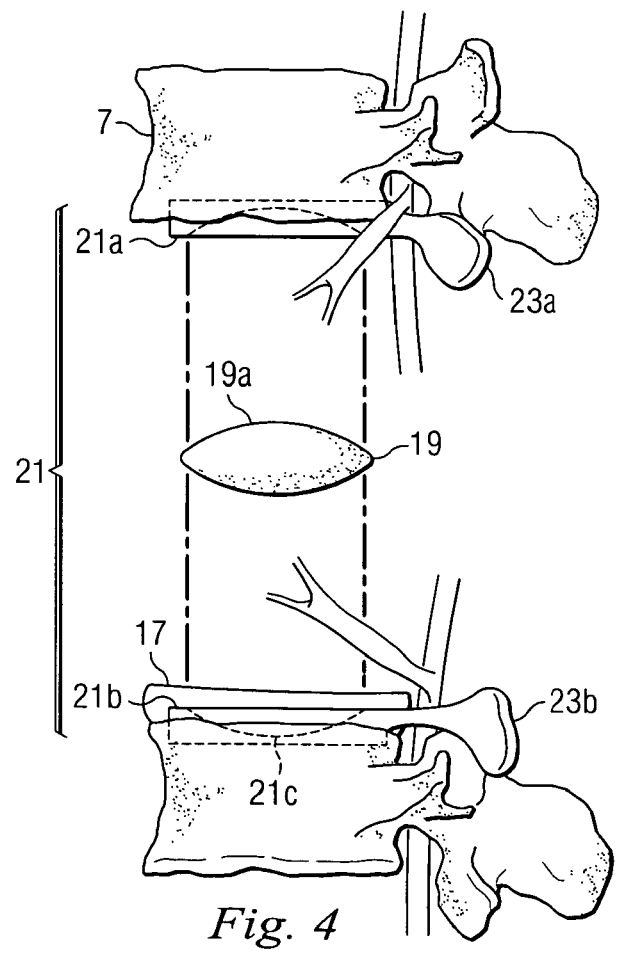
FIG. 4 is a side exploded elevation view of a portion of a lumbar spine showing a first embodiment of an artificial intervertebral joint constructed according to the principles of the disclosure.
Figure 5:
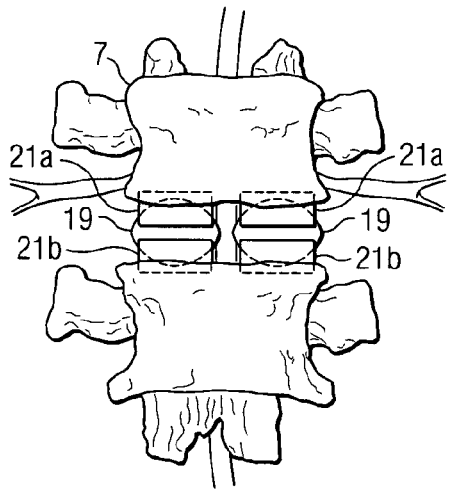
FIG. 5 is an anterior elevation view of a portion of a lumbar spine showing the superior, disc and inferior portions of the left and right halves of an assembled artificial intervertebral joint constructed according to the first embodiment of the disclosure.

FIGS. 4-7 illustrate a first exemplary embodiment of an artificial intervertebral joint. As illustrated in FIGS. 4 and 5, each joint is composed of two arthroplasty halves, each of which has a spacer or disc 19 and a retaining portion 21. The retaining portion 21 includes a first retaining portion 21a and a second retaining portion 21b. In the example illustrated in FIG. 4, the first retaining portion 21a is superior to (above) the second retaining portion 21b and the disc 19 is situated therebetween. Although the artificial intervertebral joint according to this exemplary embodiment has two halves for each of the first retaining portion and the second retaining portion, it should be understood that alternative embodiments may be implemented such that the artificial intervertebral joint has a single first retaining member, a single second retaining member and a single spacer. It should also be understood that alternative embodiments may also be carried out with arthroplasties having a first retaining portion, a second retaining portion, and/or a disc which each consist of unequal sized halves or more than two components.

Further, as illustrated in FIG. 4, the first retaining portion 21a and the second retaining portion 21b are situated between two adjacent vertebrae. More particularly, the first retaining portion may be situated along an inferior surface of the upper of the two adjacent vertebrae and the second retaining portion may be situated above a superior surface of the lower of the two adjacent vertebrae. However, it should be understood by one of ordinary skill in the art that the first retaining portion and second retaining portion are not limited to such an arrangement, and may be oriented in different positions and/or shaped differently than what is illustrated herein.

The surfaces of the retaining portions 21a, 21b of the arthroplasty that contact the remaining end plates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the implants to one or both of the endplates.

As discussed in more detail below, a significant portion of the outer annulus region 17 (see, e.g., FIGS. 4, 7B), in some embodiments about 300 degrees, may be retained on the inferior portion of the end plate, which acts as a stop retaining the lower retaining portions in place until bone ingrowth occurs to firmly attach the retaining portions to their respective vertebrae (FIG. 4 only shows a portion of the outer annulus 17 that is retained). In contrast, in conventional anterior arthroplasty about 270 degrees of the outer annulus region 17 typically is removed. In addition, pedicle screws may also be used for immediate fixation as described in more detail in connection with other embodiments discussed below.

In the various embodiments of this disclosure, the first retaining portion 21a and the second retaining portion 21b are structured so as to retain the disc 19 therebetween. For example, in the case of a disc 19 with two convex surfaces 19a, each of the first retaining portion 21a and the second retaining portion 21b may have a concave surface 21c which defines a space within which the disc 19 may be retained. For example, in the exemplary embodiment shown in FIG. 4, the upper convex surface 19a of the disc 19 fits within the concavity defined by the concave surface 21c of the first retaining portion 21a and the lower convex surface 19b of the disc 19 fits within the concavity defined by the concave surface 21c of the second retaining portion 21b.

Figure 6:
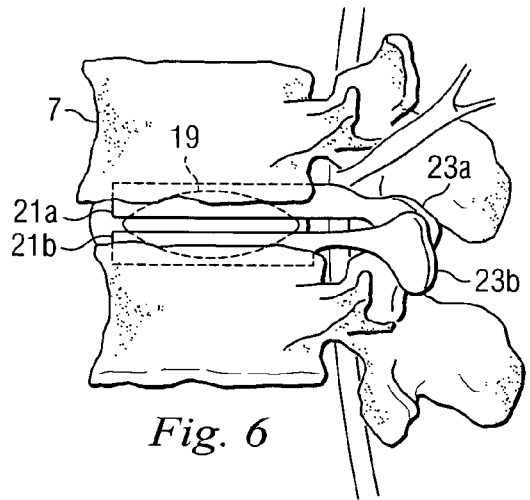
FIG. 6 is a side elevation view of the right half of the artificial intervertebral joint shown in FIG. 5.

FIG. 5 illustrates an anterior view of an exemplary assembled artificial intervertebral joint with both arthroplasty halves in place, and FIG. 6 shows a side view of the assembled artificial intervertebral joint shown in FIG. 5. As illustrated in FIGS. 5 and 6, the disc 19 is retained between the first retaining portion 21a and the second retaining portion 21b. It should be understood that although the disc 19 may be held between the first retaining portion 21a and the second retaining portion 21b, the disc 19 is free to slidably move within the space defined by the corresponding surfaces 21a of the first retaining portion 21a and the second retaining portion 21b. In this manner, limited movement between the adjacent vertebrae is provided.

In the exemplary embodiment illustrated in FIGS. 4, 5 and 6, the disc 19 is a separate component which is inserted between the first retaining portion 21a and the second retaining portion 21b. However, as discussed below, it should be understood that the spacer or disc 19 may be integrally formed with or integrated into in one or both of the first retaining portion 21a and the second retaining portion 21b.

Figure 7A:
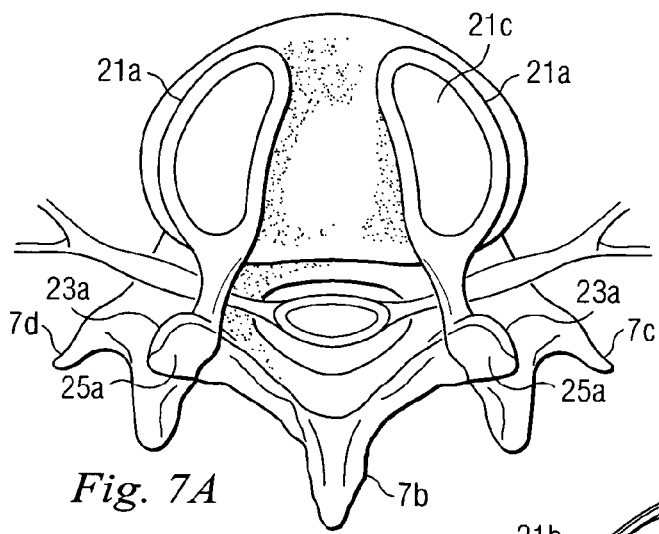
FIG. 7A is a transverse, bottom-up-view of a portion of a lumbar spine showing the superior portion of the artificial intervertebral joint illustrated in FIG. 4.
Figure 7B:
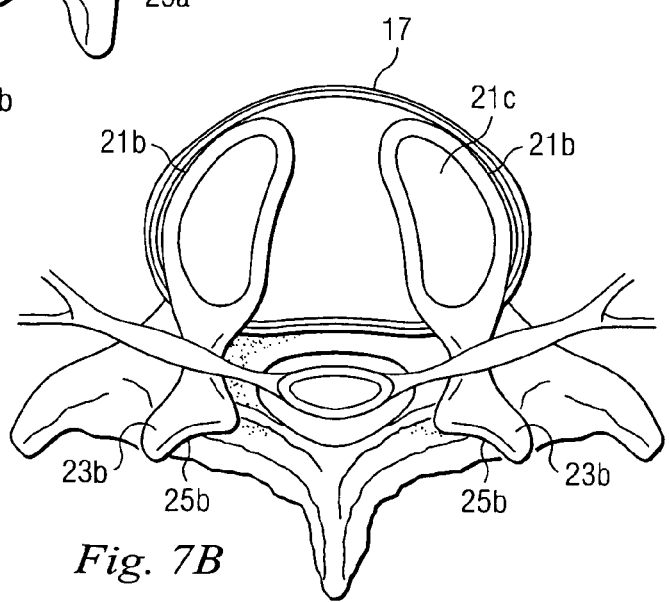
FIG. 7B is a transverse, top-down-view of a portion of a lumbar spine showing the inferior portion of the artificial intervertebral joint illustrated in FIG. 4.
Figure 8:
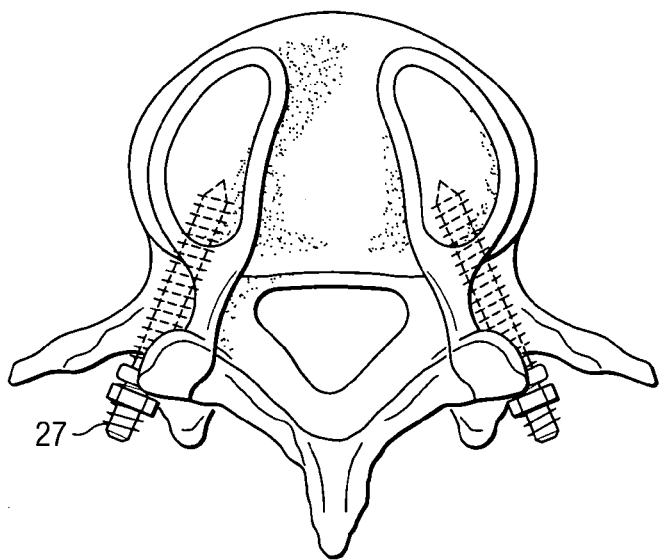
FIG. 8 is a transverse, bottom-up-view of a portion of a lumbar spine showing a second embodiment of a superior portion of an artificial intervertebral joint in which pedicle screws are used to assist in implantation.
Figure 9:
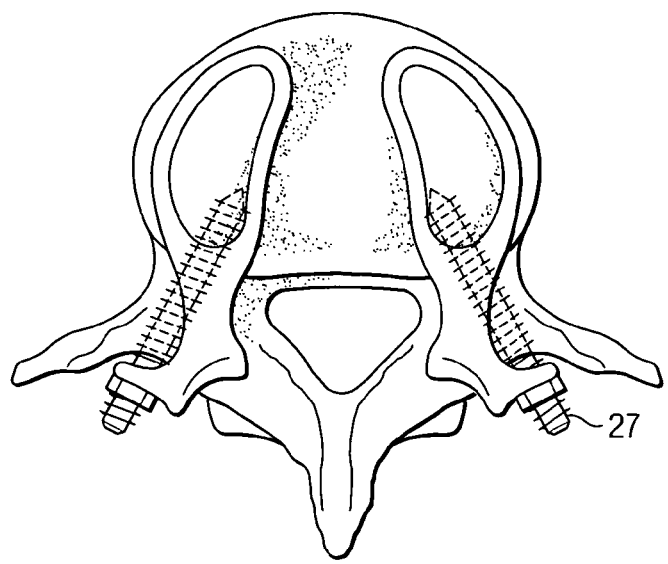
FIG. 9 is a transverse, top-down-view of a portion of a lumbar spine showing a second embodiment of an inferior portion of an artificial intervertebral joint in which pedicle screws are used to assist in implantation.
Figure 10:
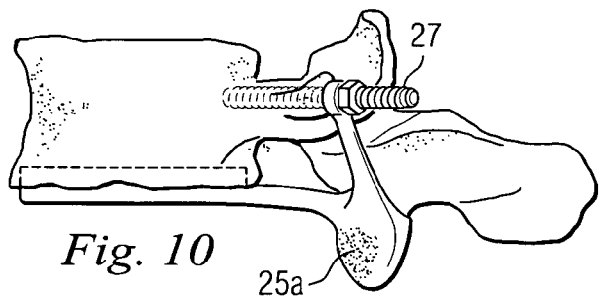
FIG. 10 is a lateral view of a portion of a lumbar spine showing the superior portion of the artificial intervertebral joint shown in FIG. 8 with one of the pedicle screws being visible.
Figure 11:
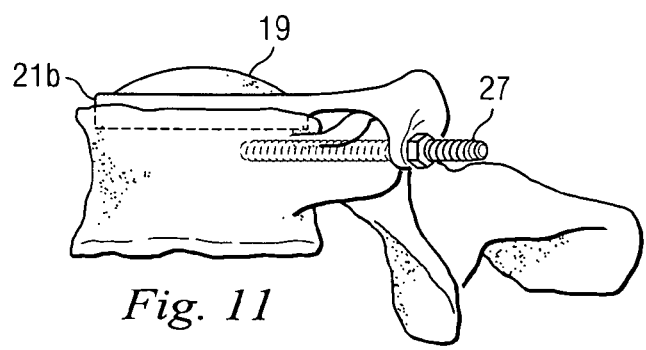
FIG. 11 is a lateral view of a portion of a lumbar spine showing the inferior and integrated disc portions of an artificial integral intervertebral joint shown in FIG. 9 with one of the pedicle screws being visible.
Figure 12:
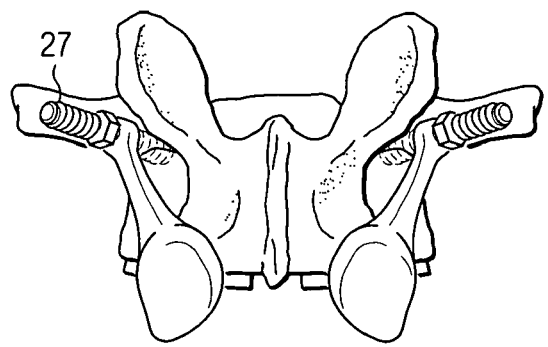
FIG. 12 is a posterior view of a portion of a lumbar spine showing the superior portion of the artificial intervertebral joint shown in FIG. 8 with two pedicle screws being visible.
Figure 13:
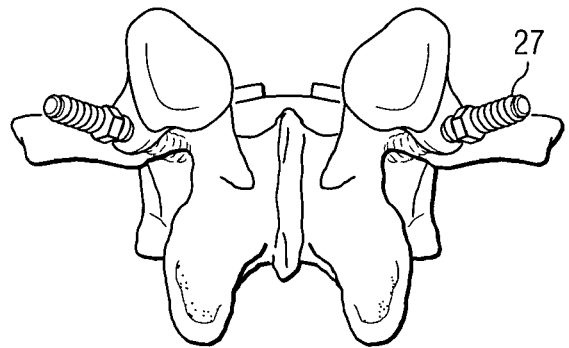
FIG. 13 is a posterior view of a portion of a lumbar spine showing the inferior portion of the artificial intervertebral joint shown in FIG. 9 with two pedicle screws being visible.

In the exemplary embodiment of the disclosure, as illustrated best in FIGS. 4, 6, 7A and 7B, each of the retaining portions of the artificial intervertebral joint includes a first artificial facet component 23a and a second artificial facet component 23b. As shown in FIGS. 7A and 7B, the first artificial facet component 23a has a face 25a and the corresponding second artificial facet component 23b has a face 25b configured such that the face 25a matingly fits with the face 25b to stabilize adjacent vertebrae while preserving and guiding the mobility of each vertebrae with respect to the other vertebrae. Each set of the upper and lower retaining portions 21a, 21b may have a pair of facet components 23a, 23b, which together define a facet joint. For a total joint replacement with facets according to this embodiment, the left and right arthroplasties would define two adjacent facet joints when viewed from the posterior.

Regardless of whether artificial facet joints are provided, the respective upper and lower retaining portions associated with the left and right halves of the arthroplasty may be completely independent from the other. That is, as shown in FIG. 7A, for example, the first retaining portions 21a associated with each half are not in direct contact with each other. The same is true with respect to the second retaining portions 21b shown in FIG. 7B. However, it should be understood by one of ordinary skill in the art that, even in the embodiment of the disclosure which includes artificial facet joints, at least a portion of the first retaining portions 21a of each half and/or at least a portion of the second retaining portions 21b of each half may directly contact and/or be connected to each other as described in more detail in connection with the discussion of FIGS. 17-18.

Further, in the various embodiments of the disclosure, the disc 19, the first retaining portion 21a and the second retaining portion 21b may be made of any appropriate material which will facilitate a connection that transmits compressive and tensile forces while providing for the aforementioned slidable motion in a generally transverse direction between each of the adjacent surfaces. For example, in the first embodiment, the first retaining portion 21a and the second retaining portion 21b may be typically made from any metal or metal alloy suitable for surgical implants such as stainless steel, titanium, and cobalt chromium, or composite materials such as carbon fiber, or a plastic material such as polyetheretherketone (PEEK) or any other suitable materials. The disc may be made from plastic such as high molecular weight polyethylene or PEEK, or from ceramics, metal, and natural or synthetic fibers such as, but not limited to, carbon fiber, rubber, or other suitable materials. Generally, to help maintain the sliding characteristic of the surfaces, the surfaces may be polished and/or coated to provide smooth surfaces. For example, if the surfaces are made of metal, the metal surfaces may be polished metal.

FIGS. 8-14 illustrate a second embodiment of an artificial intervertebral joint. Only features that differ from the first embodiment are discussed in detail herein. In the second exemplary embodiment, securing components, such as, for example, pedicle screws 27 are provided to provide a more secure and immediate connection between each of the first retaining portion 21a and/or the second retaining portion 21b to the corresponding vertebra. In addition, this embodiment illustrates a disc 19 which is integrated with one of the retaining portions, here lower retaining portion 21b. Disc 19 may be integrally formed from the same material as its retaining portion, but also may be separately formed from similar or dissimilar materials and permanently connected thereto to form an integral unit. In this embodiment, the disc 19 and the retaining portions may be all formed from metal.

Figure 15:
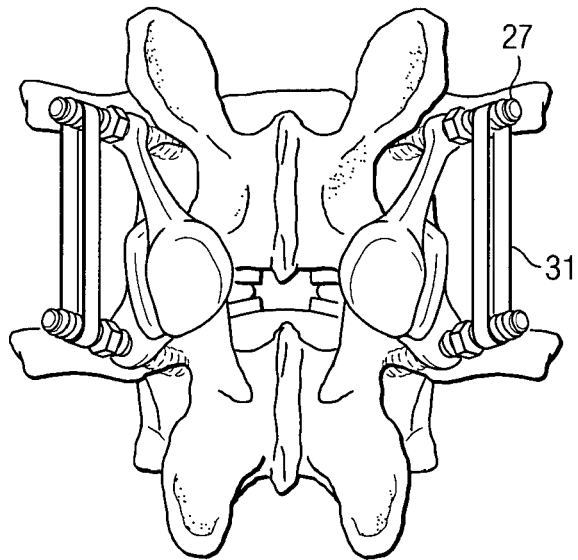
FIG. 15 is a posterior view of a portion of a lumbar spine showing a third embodiment of the inferior, disc and superior portions of an artificial intervertebral joint in which tension bands are used.
Figure 16:
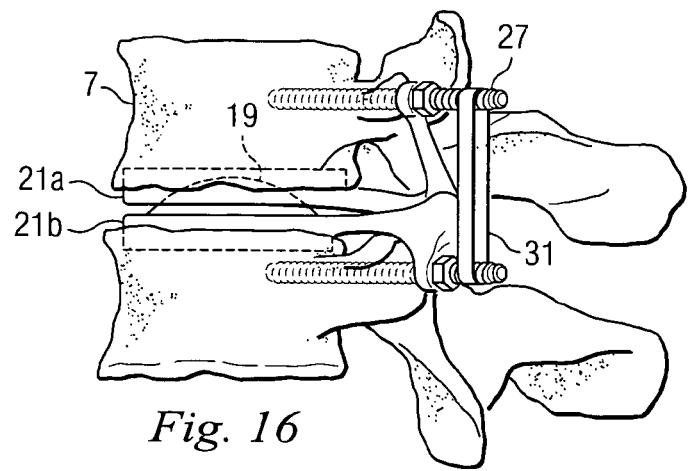
FIG. 16 is a side elevation view of a portion of a lumbar spine showing the third embodiment in which tension bands are used in an assembled position.

FIGS. 15 and 16 illustrate a third embodiment of an artificial intervertebral joint. In the third exemplary embodiment, additional securing components, such as, for example, tension bands 31 are provided to supplement or replace the function of posterior ligaments that limit the mobility between adjacent vertebrae by securing the first retaining portion 21a to the second retaining portion 21b. As shown in FIGS. 15-16, posterior tension bands 31 may be provided by wrapping them around the corresponding pedicle screws 27 or other convenient attachment points.

Figure 17:
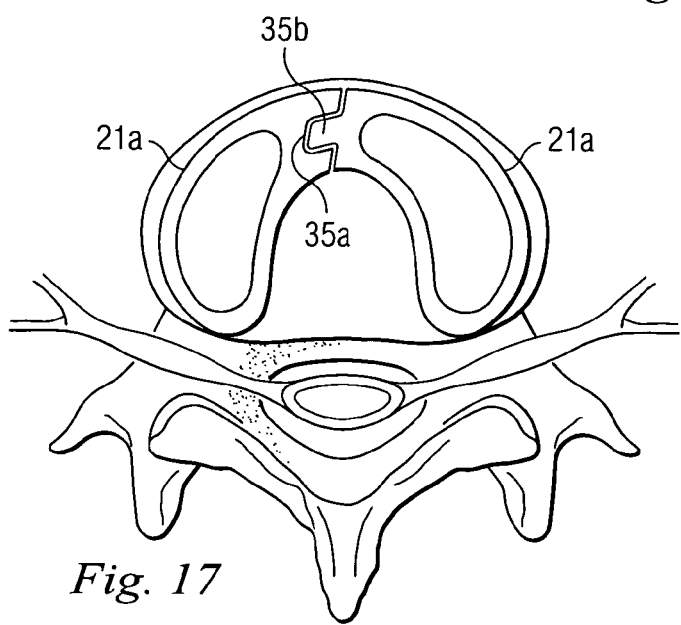
FIG. 17 is a transverse, bottom-up-view of a portion of a lumbar spine showing the superior portion of a fourth embodiment of an artificial intervertebral joint constructed according to the principles of the disclosure in which the facet joints are not replaced.
Figure 18:
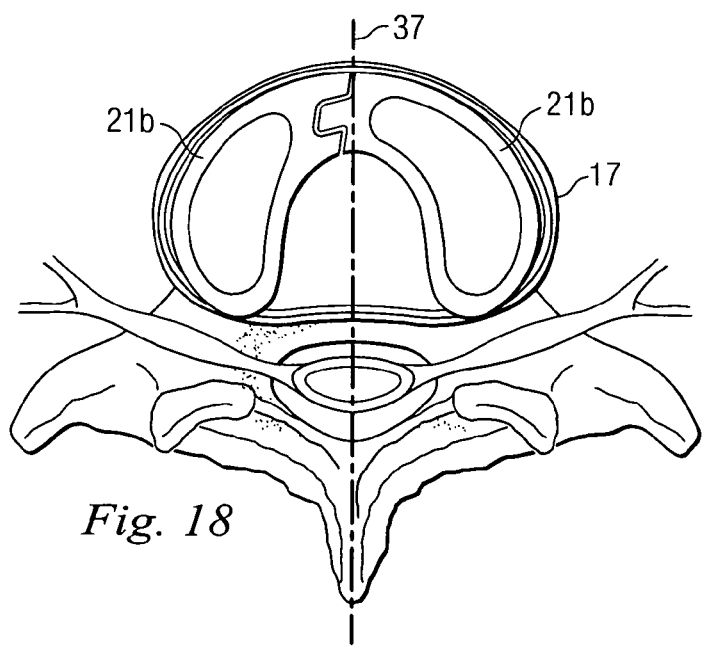
FIG. 18 is a transverse, top-down-view of a portion of a lumbar spine showing the inferior portion of the fourth embodiment of an artificial intervertebral joint.

FIGS. 17 and 18 illustrate a fourth embodiment of an artificial intervertebral joint. In the exemplary embodiment illustrated in FIGS. 17 and 18, the artificial intervertebral joint may have all of the features discussed above except for artificial facet components. In this embodiment, the natural facet joints remain. The ligamentous tension band may also be left intact in some embodiments. In addition, this embodiment includes a specific example of an anterior midline connection between respective upper and lower retaining portions, which assists in maintaining the placement of the first retaining portion 21a and the second retaining portion 21b.

FIGS. 17 and 18 illustrate that it is possible to provide a first retaining portion 21a with a lock and key type pattern which is complemented by the corresponding mating portion provided on the second retaining portion 21b. More particularly, one half of the first retaining portion 21a has an outer boundary with a U-shaped portion 35a while the other half of the corresponding first retaining portion 21a has an outer boundary with a protruding portion 35b, which fits into the U-shaped portion 35a. As a result, each half of the first retaining portion 21a, 21b may be maintained in a predetermined position. However, the upper or lower retaining portions may fit together and/or be connected in the interbody space, e.g., near their midline anterior portions, in any manner that facilitates implantation and/or assists in providing and/or retaining the joint in a generally stable, symmetrical configuration. It may be even more important to provide such connection between the lower retaining portions due to the inward forces provided by annulus 17 remaining on the inferior end plate as shown in FIG. 18. A midline connection between the respective lower retaining portions will resist the force of the outer annulus tending to cause migration of the retaining portions toward the midline 37.

As shown in the various exemplary embodiments, other than the portions of the first and/or second retaining portions which may fit together like a lock and key to maintain the placement of the portions relative to each other, each half of the artificial intervertebral joint may be generally symmetrical about the midline 37 of the vertebrae.

Again, these exemplary embodiments are merely illustrative and are not meant to be an exhaustive list of all possible designs, implementations, modifications, and uses of the invention. Moreover, features described in connection with one embodiment of the disclosure may be used in conjunction with other embodiments, even if not explicitly stated above.

While it should be readily apparent to a skilled artisan from the discussion above, a brief description of a suitable surgical procedure that may be used to implant the artificial joint is provided below. Generally, as discussed above, the artificial intervertebral joint may be implanted into a body using a posterior transforaminal approach similar to the known TLIF or PLIF procedures. According to this approach, an incision, such as a midline incision, may be made in the patient's back and some or all of the affected disc and surrounding tissue may be removed via the foramina. Depending on whether any of the facet joints are being replaced, the natural facet joints may be trimmed to make room for the artificial facet joints. Then, the halves of the artificial intervertebral joint may be inserted piecewise through the left and right transforaminal openings, respectively. That is, the pieces of the artificial intervertebral joint including the upper and lower retaining portions, with or without facet components, and the artificial disc, if provided separately, fit through the foramina and are placed in the appropriate intervertebral space. The pieces of the artificial joint may be completely separated or two or more of them may be tied or packaged together prior to insertion through the foramina by cloth or other materials known in the art. In cases where at least a portion of the outer annulus of the natural disc can be retained, the lower retaining portions of each side of the artificial intervertebral joint are inserted such that they abut a corresponding portion of the annulus. If a midline anterior connection is provided, the left and right halves of the retaining members are fitted together and held in place by the outer annulus. As such, the remaining portion of the annulus may be in substantially the same place as it was prior to the procedure.

Further, in the cases where the annulus of the natural disc must be removed completely or this is insufficient annulus remaining, it is possible, for example, to use the embodiment of the disclosure where the pedicle screws are implemented so as to be assured that the pieces of the artificial intervertebral joint remain in place. It should be understood by one of ordinary skill in the art that the artificial joint could be implanted via an anterior approach or a combined anterior and posterior approach, although the advantages of a posterior procedure would be limited. For example, some of the pieces of the artificial intervertebral joint may be inserted from an anterior approach and others posteriorly. The anteriorly and posteriorly placed portions could be fitted together similar to the embodiment shown in FIGS. 17 and 18.

Figure 19:
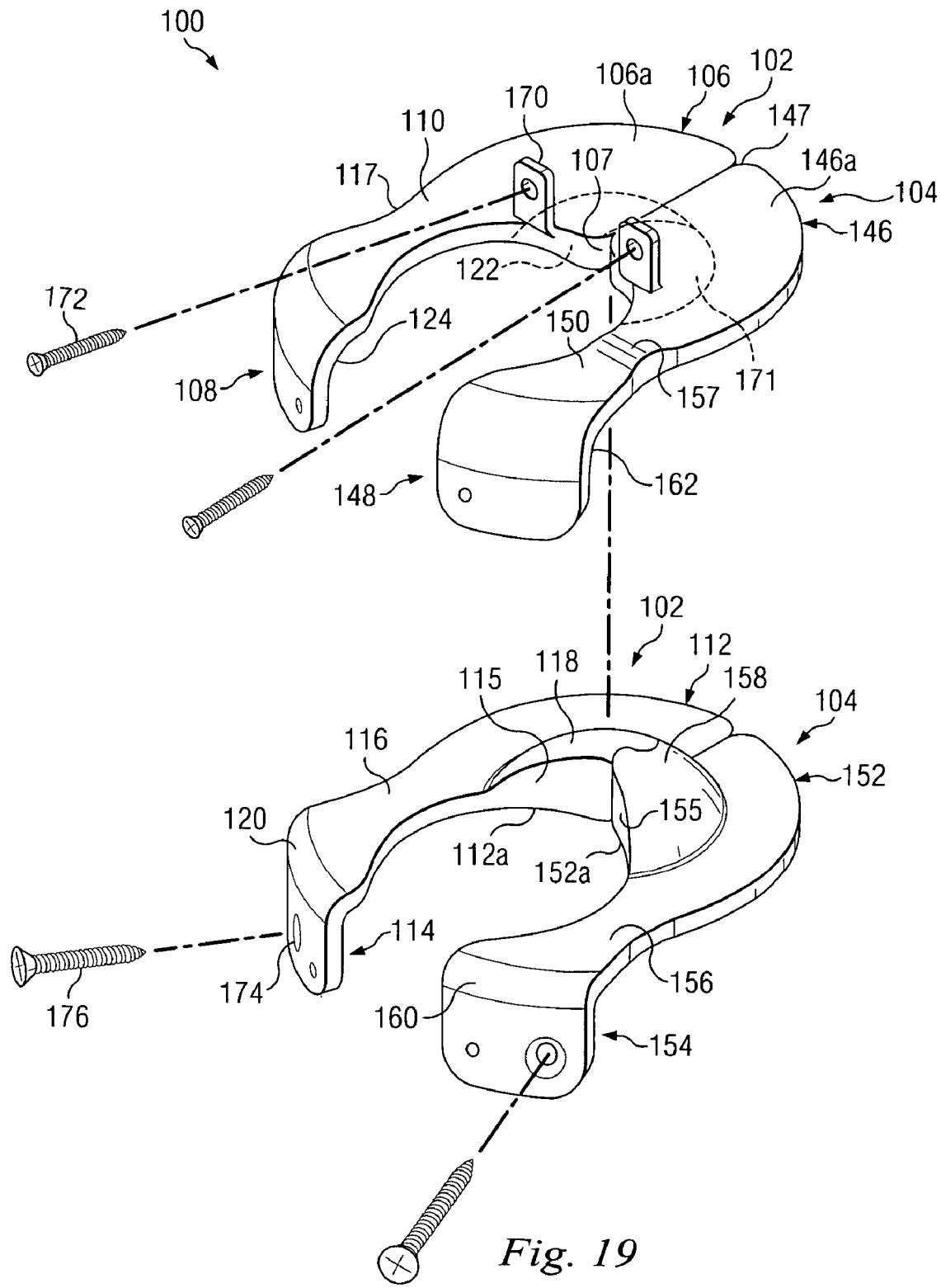
FIG. 19 is an exploded perspective view of another embodiment of the present disclosure.
Figure 20:
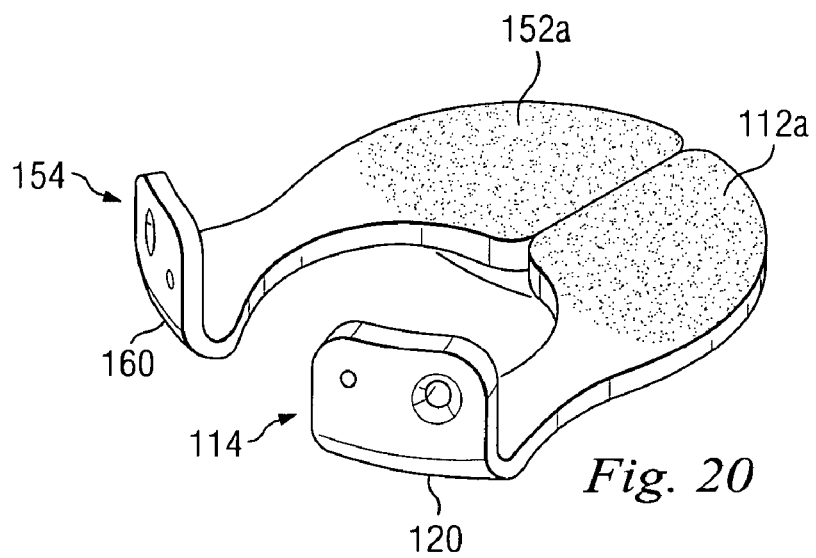
FIG. 20 is a second perspective view of the embodiment of FIG. 19.
Figure 21:
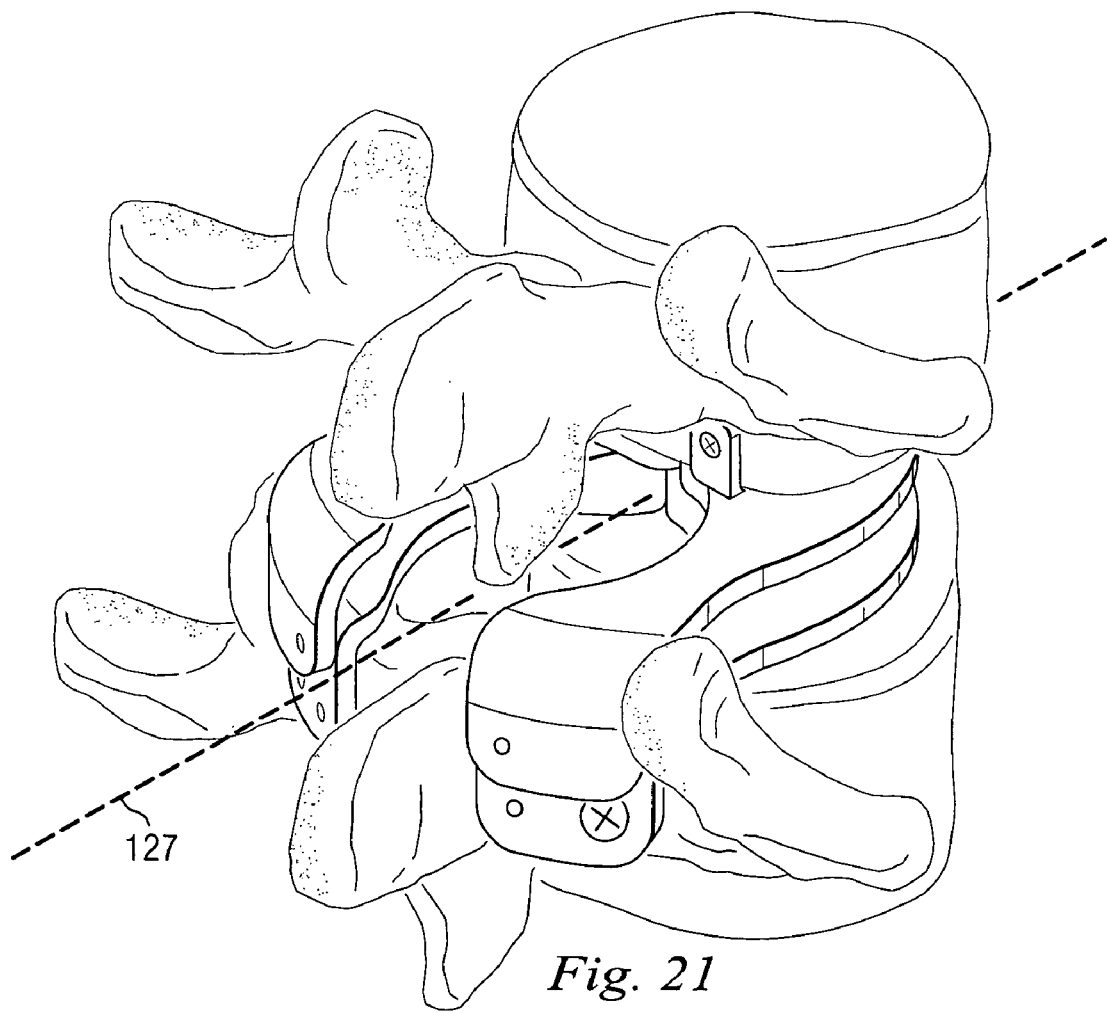
FIG. 21 is a third perspective view of the embodiment of FIG. 19.

Referring now to FIGS. 19, 20, and 21, in this embodiment, an artificial intervertebral joint 100 may include two arthroplasty halves 102, 104 which may be inserted between the vertebrae 7, 9. The arthroplasty half 102 may be an articulating joint replacement assembly and may include a rostral anterior component 106, a rostral posterior joint component 108, and a rostral bridge 110 extending between the anterior component 106 and the posterior component 108. The rostral anterior component 106 may further include an interlocking wall 107. The arthroplasty half 102 may further include a caudal anterior joint component 112, a caudal posterior joint component 114, and a caudal bridge 116 extending between the anterior component 112 and the posterior component 114. The caudal anterior component 112 may further include an interlocking wall 115. The rostral anterior joint component 106 may include a bone contacting surface 106a, and the caudal anterior joint component 112 may include a bone contacting surface 112a.

The terms "rostral" and "caudal" are used in some embodiments to describe the position of components of the embodiments. While rostral is typically used in the art to describe positions toward the head and caudal is used to describe positions toward the tail or foot, as used herein, rostral and caudal are used simply as modifiers for the relative locations of components of the illustrated embodiments. For example, rostral components may be on one side of an illustrated joint, and caudal may be on another side of the joint. Components labeled as rostral or caudal to describe an illustrated embodiment are not intended to limit the orientation of a device or application of a method relative to a patient's anatomy, or to limit the scope of claims to any device or method.

In this embodiment, the rostral bridge 110 may include a jog 117 to create an exit portal and an artificial foramen for the exiting nerve root. Either of the bridges 110, 116, but particularly the caudal bridge 116, may be a "super" or artificial pedicle which may supplement or replace a natural pedicle. Also in this embodiment, the caudal anterior joint component 112 may include a caudal articulating surface such as a curved protrusion 118, and the caudal posterior joint component 114 may include a posterior articulating portion 120. The rostral anterior joint component 106 may include a rostral articulating surface such as an anterior socket 122 configured to receive the curved protrusion 118. A radius of curvature for the curved protrusion 118 may closely match the radius of curvature for the anterior socket 122 to create a highly constrained ball and socket type engagement. In an alternative embodiment, by increasing the radius of curvature for the socket relative to the radius of the curved protrusion, the curved protrusion may be permitted to translate within the socket.

The rostral posterior joint component 108 may include a posterior socket 124 configured to engage the posterior articulating portion 120. A radius of curvature for the posterior articulating portion 120 may be smaller than a radius of curvature for the posterior socket 124, thereby permitting motion and limiting binding between the posterior joint components 108, 114. The radii of curvature for the posterior socket 124 and the posterior articulating portion 120 may emanate from a common center of rotation for the arthroplasty half 102. In this embodiment, the radius of curvature for the posterior socket 124 is relatively large, and the resulting joint is loosely constrained. In an alternative embodiment, a tight radius of curvature for the posterior protrusion of the caudal posterior component matched with a rostral posterior component having a tight radius of curvature may create a tightly constrained posterior joint.

The arthroplasty half 104 may be an articulating joint replacement assembly and may include a rostral anterior joint component 146, a rostral posterior joint component 148, and a rostral bridge 150 extending between the anterior component 146 and the posterior component 148. The rostral anterior component 146 may further include an interlocking wall 147. The arthroplasty half 104 may further include a caudal anterior joint component 152, a caudal posterior joint component 154, and a caudal bridge 156 extending between the anterior component 152 and the posterior component 154. The caudal anterior component 152 may further include an interlocking wall 155. The rostral anterior joint component 146 may include a bone contacting surface 146a and the caudal anterior joint component 152 may include a bone contacting surface 152a.

In this embodiment, the rostral bridge 150 may include a jog 157 to create an exit portal and an artificial foramen for the exiting nerve root. Also in this embodiment, the caudal anterior joint component 152 may include a caudal articulating surface such as a curved protrusion 158. The rostral anterior joint component 146 may include a rostral articulating surface such as an anterior socket 171 configured to receive the curved protrusion 158. A radius of curvature for the curved protrusion 158 may closely match the radius of curvature for the anterior socket 171 to create a highly constrained ball and socket type engagement. In an alternative embodiment, by increasing the radius of curvature for the socket relative to the radius of the curved protrusion, the curved protrusion may be permitted to translate within the socket.

Also in this embodiment, the caudal posterior joint component 154 may include a posterior articulating portion 160. The rostral posterior joint component 148 may include a posterior socket 162 configured to engage the posterior articulating portion 160. A radius of curvature for the posterior articulating portion 160 may be smaller than a radius of curvature for the posterior socket 162, thereby permitting motion and limiting binding between the posterior joint components 148, 154. The radii of curvature for the posterior socket 162 and the posterior articulating portion 160 may emanate from a common center of rotation for the arthroplasty half 104. In this embodiment, the radius of curvature for the posterior socket 162 is relatively large, and the resulting joint is loosely constrained. In an alternative embodiment, a tight radius of curvature for the posterior protrusion of the caudal posterior component matched with a rostral posterior component having a tight radius of curvature may create a tightly constrained posterior joint.

The size and shape of the anterior components 106, 112, 146, 152 and the bridge components 110, 116, 150, 156 may be limited by the constraints of a posterior or transforaminal surgical approach. For example, the anterior components 106, 112, 146, 152 may be configured to cover a maximum vertebral endplate area to dissipate loads and reduce subsidence while still fitting through the posterior surgical exposure, Kambin's triangle, and other neural elements. The width of the bridge components 110, 116, 150, 156 are also minimized to pass through Kambin's triangle and to co-exist with the neural elements.

The arthroplasty halves 102, 104 may further includes features for securing to the vertebrae 7, 9. It is understood, however, that in an alternative embodiment, the fixation features may be eliminated. The arthroplasty half 104 may include fixation features substantially similar to arthroplasty half 102 and therefore will not be described in detail. The arthroplasty half 102 may include a connection component 170 extending rostrally from the rostral anterior joint component 106. The connection component 170 in this embodiment includes an aperture adapted to receive a bone fastener such as a screw 172. The orientation of the connection component 170 permits interbody fixation of the screw 172 to the cylindrical vertebral body 7a.

Arthroplasty half 102 may further include a connection component 174 attached to or integrally formed with the caudal posterior joint component 114. The connection component 174 in this embodiment includes an aperture adapted to receive a bone fastener such as a screw 176. The orientation of the connection component 174 permits the screw 176 to become inserted extrapedicularly such that the screw travels a path angled or skewed away from a central axis defined through a pedicle. Extrapedicular fixation may be any fixation into the pedicle that does not follow a path down a central axis defined generally posterior-anterior through the pedicle. In this embodiment, the screw passes through a lateral wall of the pedicle and may achieve strong cortical fixation. In all embodiments, the screws may be recessed so as not to interfere with articulations, soft tissues, and neural structures.

Figure 14:
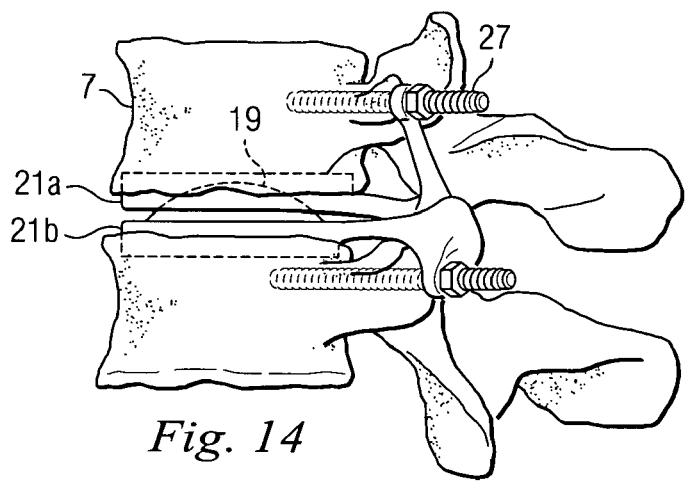
FIG. 14 is a side elevation view of a portion of a lumbar spine showing the second embodiment with pedicle screws in an assembled position.

In an alternative embodiment, for example as shown in FIG. 14, a connection component extending from the posterior component 114 may be oriented to permit the screw to become inserted intrapedicularly such that the screw travels a path generally along the central axis through the pedicle. In still another alternative embodiment, the posterior connection component may connect to the generally cylindrical body portion 9a. It is understood that in other alternative embodiments, the connection components may extend at a variety of angles, in a variety of directions from the various components of the arthroplasty half. For example, a connection component may extend from the rostral bridge rather than the rostral anterior joint component.

As shown in FIGS. 19, 20, and 21, the rostral components 106, 108, 110 of the articulating joint replacement assembly 102 are integrally formed with rigid connections between the components. It is understood that in a modular alternative embodiment, these components may be removably coupled to one another. For example, the rostral anterior joint component may be installed separate from the bridge. After the anterior component is in place, the bridge may be attached to the anterior component by any fastening mechanism known in the art, for example a threaded connection, a bolted connection, or a latched connection. A modular rostral posterior component may then be attached by a similar fastening mechanism to the bridge to complete the rostral portion of the arthroplasty half. Likewise, the caudal components may be modular.

The arthroplasty halves 102, 104 may be formed of any suitable biocompatible material including metals such as cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the arthroplasty halves 102, 104 may be formed of different materials thus permitting metal on metal, metal on ceramic, metal on polymer, ceramic on ceramic, ceramic on polymer, or polymer on polymer constructions.

Bone contacting surfaces of the arthroplasty halves 102, 104 may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the arthroplasty halves 102, 104 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The artificial intervertebral joint 100 may be installed between the vertebrae 7, 9 as will be described below using a bilateral delivery. Generally, the artificial intervertebral joint 100 may be implanted into a body using a posterior transforaminal approach similar to the known TLIF or PLIF procedures. PLIF approaches are generally more medial and rely on more retraction of the traversing root and dura to access the vertebral interspace. The space between these structures is known as Kambin's triangle. TLIF approaches are typically more oblique, requiring less retraction of the exiting root, and less epidural bleeding with less retraction of the traversing structures. It is also possible to access the interspace using a far lateral approach, above the position of the exiting nerve root and outside of Kambin's triangle. In some instances it is possible to access the interspace via the far lateral without resecting the facets. Furthermore, a direct lateral approach through the psoas is known. This approach avoids the posterior neural elements completely. Embodiments of the current invention are anticipate that could utilize any of these common approaches.

According to at least one of these approaches, an incision, such as a midline incision, may be made in the patient's back and some or all of the affected disc and surrounding tissue may be removed via the foramina. The superior endplate surface of the vertebra 9 may be milled, rasped, or otherwise resected to match the profile of the caudal anterior bone contacting surface 112a, to normalize stress distributions on the superior endplate surface of the vertebra 9, and/or to provide initial fixation prior to bone ingrowth. The preparation of the endplate of vertebra 9 may result in a flattened surface or in surface contours such as pockets, grooves, or other contours that may match corresponding features on the bone contacting surface 112a. The inferior endplate of the vertebra 7 may be similarly prepared to receive the rostral anterior joint component 106 to the extent allowed by the exiting nerve root and the dorsal root ganglia. Depending on whether any of the facet joints are being replaced, the natural facet joints of vertebrae 7, 9 may be trimmed to make room for the posterior components 108, 114.

The articulating joint replacement assembly 102 of the artificial intervertebral joint 100 may then be inserted piecewise through, for example, the left transforaminal exposure. That is, the pieces of the articulating joint replacement assembly 102 including the rostral and caudal anterior joint components 106, 112 respectively are fit through the foramina and are placed in the appropriate intervertebral disc space between the generally cylindrical bodies 7a, 9a. The anterior joint components 106, 112 may be delivered along a curved path similar to that used in a "kidney bean" TLIF graft. Within the intervertebral disc space, the anterior joint components 106, 112 may be positioned such that the anterior socket 122 is engaged with the curved protrusion 118 to form one lateral half of a single, unitized ball and socket style joint. The joint formed by the anterior socket 122 and the curved protrusion 118 may abut a central anterior-posterior axis 127 through the intervertebral disc space. As described, the anterior articulation provided by the anterior socket 122 engaged with the curved protrusion 118 may be completed with unilateral delivery. If the articulating joint replacement assembly 104 cannot be inserted, the articulating joint replacement assembly 102 may function on its own. During insertion, the pieces of the articulating joint replacement assembly 102 may be completely separated or two or more of them may be tied or packaged together prior to insertion through the foramina by cloth or other materials known in the art. In cases where at least a portion of the outer annulus of the natural disc can be retained, the caudal anterior joint components may be inserted such that they abut a corresponding portion of the annulus.

The bridges 110, 116 may extend posteriorly from the anterior joint components 106, 112, respectively and posteriorly from the intervertebral disc space. The posterior components 108, 114 may be positioned posteriorly of the intervertebral disc space with the posterior socket 124 engaged with the posterior articulating portion 120. These posterior components 108, 114 may replace or supplement the function of the natural facet joints. Similar positioning may be completed for the components of the arthroplasty half 104. In addition to joining the anterior and posterior components, the bridges 110, 116, 150, 156 may serve to prevent subsidence. By crossing onto either the pedicle (for caudal bridges 116, 156) or the posterior wall of the apophyseal ring (for rostral bridges 110, 150) greater surface area is created and bone subsidence may be reduced.

The articulating joint replacement assembly 104 of the artificial intervertebral joint 100 may then be inserted piecewise through a contralateral exposure, for example, a right transforaminal exposure. That is, the pieces of the articulating joint replacement assembly 104 including the rostral and caudal anterior joint components 146, 152 respectively fit through the contralateral foramina and are placed in the appropriate intervertebral disc space between the generally cylindrical bodies 7a, 9a. The anterior joint components 146, 152 may also be delivered along a curved path similar to that used in a "kidney bean" TLIF graft or any other path that accommodates the shape of the components. The pieces of the articulating joint replacement assembly 104 may be completely separated or two or more of them may be tied or packaged together prior to insertion through the foramina by cloth or other materials known in the art.

Within the intervertebral disc space, the anterior joint components 146, 152 may be positioned such that the anterior socket 171 is engaged with the curved protrusion 158 to form one lateral half of a single, unitized ball and socket style joint. The joint formed by the anterior socket 171 and the curved protrusion 158 may abut the central anterior-posterior axis 127 through the intervertebral disc space.

Also within the intervertebral disc space, the anterior joint components 146, 152 may be connected to the anterior joint components 106, 112, respectively. In this embodiment, the interlocking wall 115 of the caudal anterior joint component 112 may be placed into engagement with the interlocking wall 155 of the caudal anterior joint component 152. Curved protrusion 118 may thus become connected to curved protrusion 158, which in this embodiment may result in the formation of single kidney-shaped protrusion centered about the axis 127. The rostral anterior joint component 106 may be similarly positioned with respect to the rostral anterior joint component 146, with the interlocking wall 122 engaged with the interlocking wall 147. Anterior socket 122 may thus become connected to anterior socket 171, which in this embodiment may result in the formation of a single kidney-shaped recess centered about the axis 127. All together, the joint formed by the anterior socket 122 with the curved protrusion 118 and the joint formed by the anterior socket 171 with the curved protrusion 158 form a single unitized intervertebral joint centered about the axis 127. This single unitized intervertebral joint may allow for a common center of rotation for the various components of the artificial joint 100, including the posterior joints. The various articulating surfaces of the joint 100 may be formed by concentric spheres, such that motions in both the anterior joint and the posterior joints occur about a common point.

In an alternative embodiment, only the rostral joint components may be connected. In another alternative embodiment, only the caudal joint components may be connected. In another alternative, the contralateral exposure may be abandoned if problems occur during the surgery. Thus, the arthroplasty may be completed with the unilateral delivery of only the articulating joint replacement assembly 102.

The bridges 150, 156 may extend posteriorly from the anterior joint components 146, 152 and posteriorly from the intervertebral disc space. The posterior components 148, 154 may be positioned posteriorly of the intervertebral disc space with the posterior socket 162 engaged with the posterior articulating portion 160. These posterior components 148, 154 may replace or supplement the function of the natural facet joints.

After installation, the articulating joint replacement assembly 102 and the articulating joint replacement assembly 104 may be secured to vertebrae 7, 9. The screw 172 may be inserted through the connection component 170 and into the generally cylindrical body 7a. The screw 176 may be inserted through the connection component 174 and may be affixed extrapedicularly to the vertebra 9, for example, the screw 176 may pass through a lateral wall of the pedicle to achieve strong cortical fixation. Corresponding fasteners may be used to secure the articulating joint replacement assembly 104. It is understood that the screws may be implanted either after the entire arthroplasty half has been implanted or after each of the rostral and caudal component has been implanted.

As installed, the unitized anterior ball and socket type joint created by the anterior joint components 106, 112, 146, 152 may be relatively stable and self-centering. Both the anterior and the posterior joints allow the arthroplasty halves 102, 104 to resist shear forces, particularly anterior-posterior forces. Movement of the rostral anterior joint component 106 relative to the caudal anterior joint component 112 may be limited by the displacement of the posterior articulating portion 120 within the posterior socket 124. For example, lateral translation of the rostral anterior joint component 106 relative to the caudal anterior joint component 112 may be limited by the posterior joint. Similar constraints may arise in the arthroplasty half 104. Rotational motion about a longitudinal axis defined by the cylindrical bodies 7a, 9a may be limited both by the constraint in the posterior joints and by the combined constraint provided by the two arthroplasty halves 102, 104. Further, the posterior joints may restrict any true lateral bending degree of freedom.

Pure freedom of motion may be limited to flexion-extension motion about an axis defined through the anterior joints of the articulating joint replacement assemblies 102, 104. However, under certain conditions, the joint 100 may overcome these design restrictions to permit limited lateral, rotational, and coupled movements. For example, the anterior joint components 106, 112 may become disconnected from each other and experience limited "lift-off," thereby permitting additional degrees of freedom and coupled motions beyond strict flexion-extension motion. The self-centering nature of the anterior joint may encourage reconnection and alignment after lift-off occurs. The limited disconnection of the anterior joint components 106, 112 may be accommodated by the degree of constraint in the posterior joint. For example, relatively loose constraint in the posterior joint permits greater amounts of lift-off. Some degree of constraint in the posterior joint may be useful, however, to encourage reconnection and alignment of the anterior joint.

In general, a simple, anteriorly located ball and socket joint which is tightly constrained with each component having the same or similar radii of curvature may allow flexion-extension, lateral bending, and torsion motions while resisting shear forces and limiting translation. By adding an additional highly constrained ball and socket joint to the posterior components, an additional degree of freedom may be limited, such as torsion. Additional joints may further limit degrees of freedom of motion. If the anterior or posterior joints are permitted to disconnect or disarticulate additional degrees of freedom may be permitted as described above. Changing the shape of or clearance between the ball and socket components will also permit additional degrees of motion.

Figure 22:
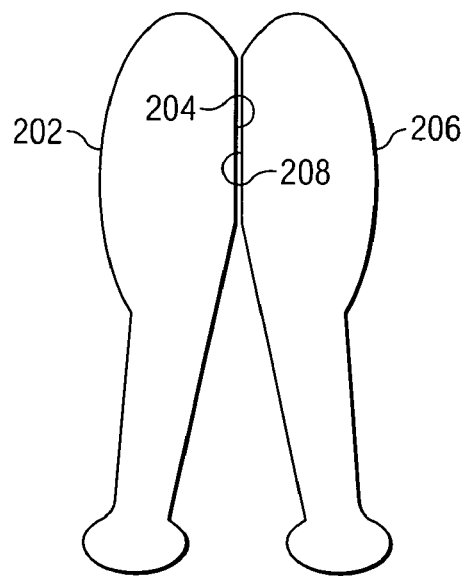
FIG. 22 is a top view of another embodiment of the present disclosure.
Figure 23:
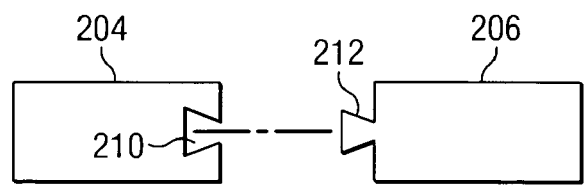
FIG. 23 is a cross-sectional view of the embodiment of FIG. 22.
Figure 24:
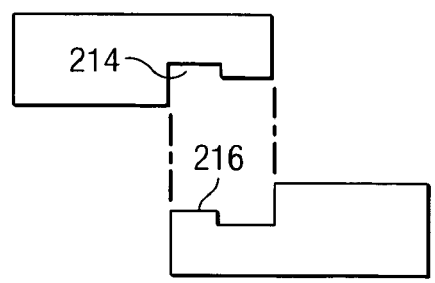
FIG. 24 is a cross sectional view of another embodiment of the present disclosure.
Figure 25:
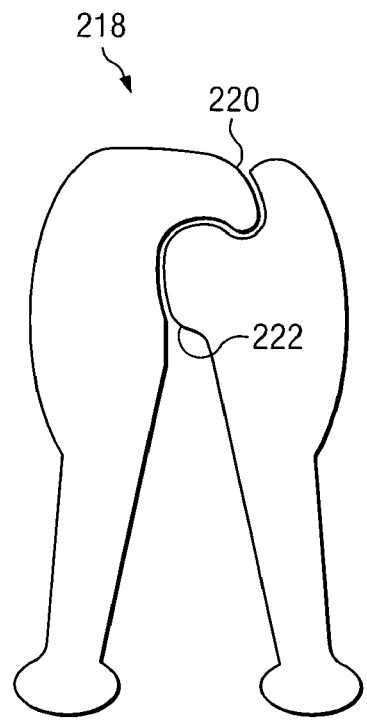
FIG. 25 is a top view of another embodiment of the present disclosure.
Figure 26:
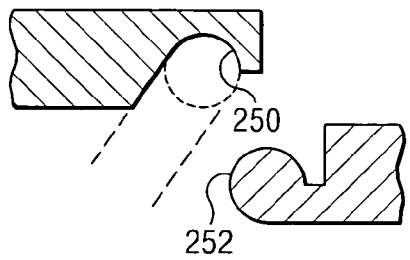
FIG. 26 is a cross-sectional view of another embodiment of the present disclosure.
Figure 27:
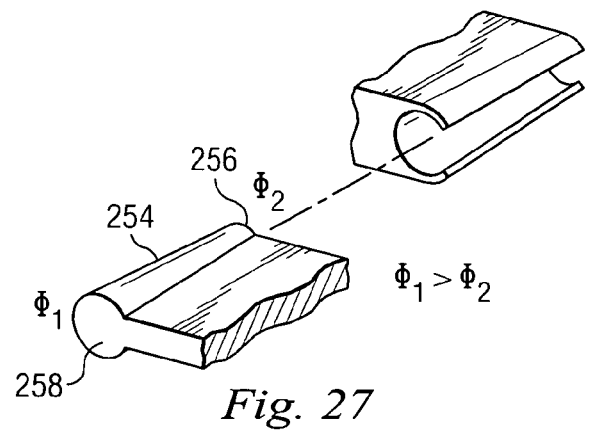
FIG. 27 is a perspective view of another embodiment of the present disclosure.

Referring now to FIGS. 22 and 23, in this embodiment, an artificial intervertebral joint may be substantially similar to artificial intervertebral joint 100 except for the differences described below. In this embodiment, a caudal anterior joint component 202 may include an interlocking wall 204, and a caudal anterior joint component 206 may include an interlocking wall 208. The interlocking wall 204 may include a connection mechanism 210, and the interlocking wall 206 may include a connection mechanism 212. In this embodiment, the connection mechanism 210 is a female component of a dove-tail connection, and the connection mechanism 212 is a male component of a dove-tail connection. In another embodiment, as shown in FIG. 24, a lap joint locking mechanism may interlock the anterior joint components. In this embodiment, a female component 214 of a lap joint locking mechanism may interlock with a male component 216 of the lap joint locking mechanism. In another embodiment, as shown in FIG. 25, a connecting mechanism 218 may include a curved, interlocking wall 220 and a curved interlocking wall 222. Similar connections may be provided for rostral anterior components. In another embodiment, as shown in FIG. 26, a semi-cylindrical locking mechanism may interlock the anterior joint components. In this embodiment, a female component 250 of the semi-cylindrical locking mechanism may interlock with a male component 252 of the semi-cylindrical locking mechanism. In another embodiment, as shown in FIG. 27, a tapered cylindrical locking mechanism may interlock the anterior joint components. In this embodiment, a male component 254 of the tapered cylindrical locking mechanism may have a diameter 256 at a distal end and a diameter 258 at a proximal end, wherein the proximal diameter 258 is larger than the distal diameter 256 and the component 254 tapers from the proximal to the distal end. The described connection mechanisms are merely examples, and any other type of mechanical or adhesive connecting mechanisms known in the art may be used as the connecting mechanism.

In an alternative embodiment, a caudal posterior joint component may include a connection component such as a round aperture. A rostral posterior joint component may include a connection component, such as an elongated aperture or slot. A bone fastener, such as a bone screw with a bushing, may be inserted through the elongated aperture and the round aperture and into the vertebra. The fastener may be allowed to translate within the elongated aperture. Accordingly, the anterior articulating joint replacement components may be permitted to articulate in a limited flexion-extension motion as the fastener translates within the elongated aperture.

Figure 28:
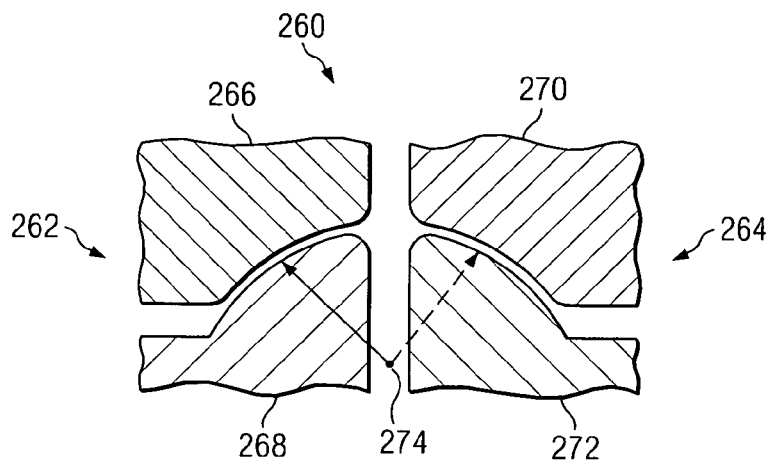
FIG. 28 is a cross-sectional view of another embodiment of the present disclosure.

Referring now to FIG. 28, in this embodiment, an artificial intervertebral joint 260 may include arthroplasty halves 262, 264. The arthroplasty half 262 may include a rostal anterior component 266 and a caudal anterior component 268. The arthroplasty half 264 may include a rostral anterior component 270 and a caudal anterior component 272. The joint 260 may be substantially similar to the joint 100 except that the rostal components 266, 270 may be unconnected. Likewise the caudal components 268, 272 may be unconnected and spaced slightly apart. Despite the gap between the halves 262, 264, the caudal anterior components 268, 272 may have a common center of curvature such that the caudal components behave as a unitized bearing.

Figure 29:
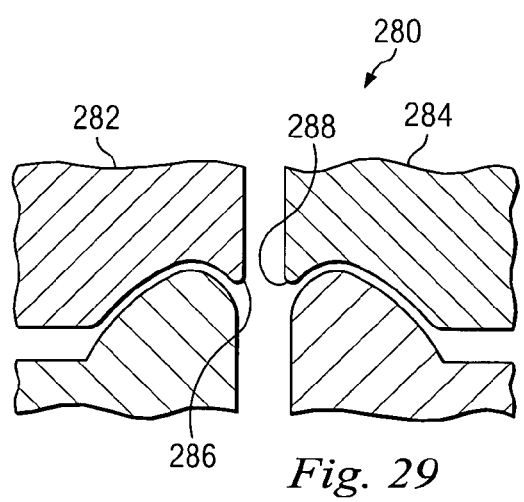
FIG. 29 is a cross-sectional view of another embodiment of the present disclosure.

Referring now to FIG. 29, in this embodiment, an artificial intervertebral joint 280 may be substantially similar to the joint 260 except that rostral components 282, 284 may include retaining features 286, 288, respectively. The retaining features 286, 288 may prevent lateral disarticulation of the caudal components.

In an alternative embodiment, any of the artificial intervertebral joints described above may further include a rostral keel extending from the rostral anterior component and/or a caudal keel extending from the caudal anterior joint component and along the caudal bridge. The rostral keel may engage the inferior endplate of the vertebral body 7a, and the caudal keel may engage the superior endplate of the vertebral body 9a and a superior face of a pedicle of vertebra 9. It is understood that the inferior endplate of the body 7a may be milled or otherwise prepared to receive the rostral keel. Likewise, the superior endplate of the body 9a and the pedicle of vertebra 9 may be milled, chiseled, or otherwise prepared to create a channel for receiving the caudal keel. The keels may help to connect to the bone and limit movement of the arthroplasty half to the desired degrees to freedom. The keels may have an angled or semi-cylindrical cross section. It is understood that more than one keel may be used on any given component.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An artificial spinal joint for creating at least a portion of a coupling between a superior vertebra and an inferior vertebra comprising:

a first arthroplasty half comprising a first articulating joint replacement component for placement in an intervertebral disc space between the superior and inferior vertebrae, a first posterior joint replacement component spaced from the first articulating joint replacement component such that when the first articulating joint replacement component is configured to be disposed in the intervertebral disc space, the first posterior joint replacement component is configured to be disposed outside the intervertebral disc space and spaced apart from the vertebral bodies of the superior vertebra and the inferior vertebra, and a first bridge component coupled between the first articulating joint replacement component and the first posterior joint replacement component, wherein the first bridge component has a length between the first articulating joint replacement component and the first posterior joint replacement component with two or more sides along the length; and a second arthroplasty half comprising a second articulating joint replacement component for placement in an intervertebral disc space between the superior and inferior vertebrae, a second posterior joint replacement component spaced from the second articulating joint replacement component such that when the second articulating joint replacement component is configured to be disposed in the intervertebral disc space, the second posterior joint replacement component is configured to be disposed outside the intervertebral disc space and spaced apart from the vertebral bodies of the superior vertebra and the inferior vertebra, and a second bridge component coupled between the second articulating joint replacement component and the second posterior joint replacement component, wherein the second bridge component has a length between the second articulating joint replacement component and the second posterior joint replacement component with two or more sides along the length;

wherein the first articulating joint replacement component is sized and shaped to engage the second articulating joint replacement component within the intervertebral disc space while the first and second posterior joint replacement components are disposed outside the intervertebral disc space and spaced apart from the vertebral bodies of the superior vertebra and the inferior vertebra;

wherein the first articulating joint replacement component includes a first rostral component in movable engagement with a first caudal component;

wherein the second articulating joint replacement component includes a second rostral component in movable engagement with a second caudal component; and wherein at least one of:
the first caudal component is connected with the second caudal component, and
the first rostral component is connected with the second rostral component.

2. The artificial spinal joint of claim 1 wherein the first and second articulating joint replacement components are engaged to form a single intervertebral joint centered about an anterior-posterior axis defined through the center of the intervertebral disc space.

3. The artificial spinal joint of claim 1 wherein the first caudal component is connected with the second caudal component.

4. The artificial spinal joint of claim 3 wherein the first caudal component comprises a first protrusion and the second caudal component comprises a second protrusion and wherein the first protrusion engaged with the second protrusion forms a single, connected kidney-shaped protrusion.

5. The artificial spinal joint of claim 1 wherein the first rostral component is connected with the second rostral component.

6. The artificial spinal joint of claim 5 wherein the first rostral component comprises a first recess and the second caudal component comprises a second recess and wherein the first protrusion engaged with the second protrusion forms a single, connected kidney-shaped recess.

7. The artificial spinal joint of claim 1 wherein the first articulating joint replacement component is engaged with the second articulating joint replacement component by a connection mechanism.

8. The artificial spinal joint of claim 7 wherein the connection mechanism is a dove tail locking mechanism.

9. The artificial spinal joint of claim 7 wherein the connection mechanism is a lap joint locking mechanism.

10. The artificial spinal joint of claim 7 wherein the connection mechanism comprises curved and interlocking portions.

11. The artificial spinal joint of claim 7 wherein the connection mechanism comprises male and female interlocking semi-cylindrical portions.

12. The artificial spinal joint of claim 7 wherein the connection mechanism comprises a male tapered cylinder adapted to engage a female tapered cylinder.

13. The artificial spinal joint of claim 1 wherein the first bridge component comprises a rostral bridge extending from the first rostral component.

14. The artificial spinal joint of claim 13 wherein the rostral bridge component comprises a jog adapted to permit passage of a neural element.

15. The artificial spinal joint of claim 1 wherein the first bridge component comprises a caudal bridge extending from the first caudal component.

16. The artificial spinal joint of claim 1 wherein the first posterior joint replacement component comprises:
a rostral posterior component, wherein the rostral posterior component includes a posterior socket and
a caudal posterior component, wherein the caudal posterior component includes a posterior articulating portion,
wherein the posterior articulating portion is adapted to articulate with the posterior socket.

17. The artificial spinal joint of claim 1 further comprising a bone fastener for attaching the artificial spinal joint to either the superior vertebra or the inferior vertebra.

18. The artificial spinal joint of claim 17 wherein the posterior joint replacement component comprises a connection component adapted to receive the bone fastener.

19. The artificial spinal joint of claim 18 wherein the bone fastener is a bone screw and the connection component is further adapted to direct the received bone screw for extrapedicular connection to the inferior vertebra.

20. The artificial spinal joint of claim 18 wherein the bone fastener is a bone screw and the connection component is further adapted to direct the received bone screw into a generally cylindrical body portion of the superior vertebra.

21. The artificial spinal joint of claim 1 wherein the first articulating joint replacement component is sized for insertion through Kambin's triangle.

22. The artificial spinal joint of claim 1 wherein the first bridge component is at least a portion of an artificial pedicle.

23. The artificial spinal joint of claim 1 wherein the first and second arthroplasty halves are joined to form a unitary, substantially U-shaped implant.

24. The artificial spinal joint of claim 1 wherein the first bridge component has four sides along its length.

25. The artificial spinal joint of claim 1 wherein the second bridge component has four sides along its length.

26. A method of implanting an artificial spinal joint, the method comprising:
creating a first exposure through a patient's back to access an intervertebral space;
creating a second exposure through the patient's back to access the intervertebral space;

delivering a first articulating assembly portion of the artificial spinal joint to the intervertebral space along a first path through the first exposure, wherein the first articulating assembly portion includes a first articulating joint replacement component and a first posterior joint portion with a first bridge having a length between the first articulating joint replacement component and the first posterior joint portion, and two or more sides along the length;

delivering a second articulating assembly portion of the artificial spinal joint to the intervertebral space along a second path through the second exposure, wherein the second articulating assembly portion includes a second articulating joint replacement component and a second posterior joint portion with a second bridge having a length between the second articulating joint replacement component and the second posterior joint portion, and two or more sides along the length; and matingly connecting the first and second articulating assembly portions to form a unitized intervertebral joint centered about an anterior-posterior axis defined through the center of the intervertebral disc space.

27. The method of claim 26 wherein the unitized intervertebral joint is a ball and socket type joint.

28. The method of claim 26,
wherein the step of delivering the first articulating assembly portion includes movably engaging a first rostral component with a first caudal component and
wherein the step of delivering a second articulating assembly portion includes movably engaging a second rostral component with a second caudal component.

29. The method of claim 26 wherein the step of matingly connecting comprises engaging the first caudal component with the second caudal component.

30. The method of claim 29 wherein the engaging the first caudal component with the second caudal component comprises creating a unitized protrusion portion of the unitized intervertebral joint.

31. The method of claim 26 wherein the step of matingly connecting comprises engaging the first rostral component with the second rostral component.

32. The method of claim 31 wherein the matingly connecting the first rostral component with the second rostral component comprises creating a unitized recess portion of the unitized intervertebral joint.

33. The method of claim 26 wherein the first path is curved.

34. The method of claim 26 wherein the second path is contralateral to the first path.

35. The method of claim 26 wherein the step of matingly connecting comprises engaging the first and second articulating assembly portions with a connection mechanism.

36. The method of claim 35 wherein the connection mechanism is a dove tail locking mechanism.

37. The method of claim 35 wherein the connection mechanism is a lap joint locking mechanism.

38. The method of claim 35 wherein the connection mechanism comprises curved and interlocking portions.

39. The method of claim 26 further comprising:
positioning a first posterior joint portion of the artificial spinal joint outside of the intervertebral space,
wherein the first posterior joint portion is connected to the first articulating assembly portion and wherein positioning a first posterior joint portion includes engaging a posterior articulating surface of the first posterior joint portion with a posterior socket of the first posterior joint portion.

40. The method of claim 39 wherein positioning the first posterior joint portion further includes restricting displacement of the posterior articulating surface within the posterior socket to restrict rotational movement in the first articulating assembly portion.

41. The method of claim 39 wherein positioning the first posterior joint portion further includes restricting displacement of the posterior articulating surface within the posterior socket within a predetermined range to limit flexion-extension movement in the first articulating assembly portion.

42. The method of claim 39 wherein positioning the first posterior joint portion further includes restricting displacement of the posterior articulating surface within the posterior socket to limit lateral bending movement in the articulating assembly portion.

43. A system for creating a coupling between a superior vertebra and an inferior vertebra, the system comprising:
a first anterior articulating assembly for implantation through a first approach into an intervertebral disc space between the superior and inferior vertebrae; and
a first posterior articulating assembly connected to the first anterior articulating assembly by a rigid bridge assembly between the first articulating assembly and the first posterior articulating assembly and spaced from the first anterior articulating assembly such that when the first articulating joint replacement component is configured to be disposed in the intervertebral disc space, the first posterior joint replacement component is configured to be disposed outside the intervertebral disc space, and spaced apart from vertebral bodies of the superior and inferior vertebrae;
wherein the rigid bridge assembly includes one or more components, each with a solid, non-cannulated structure from the first articulating assembly to the first posterior articulating assembly;
wherein the first anterior articulating assembly comprises a caudal articulating surface engaged with a rostral articulating surface wherein the engagement of the caudal and rostral articulating surfaces defines a lateral half of a ball and socket type joint; and
further wherein the lateral half of a ball and socket type joint abuts a central anterior-posterior axis through the intervertebral disc space, the ball of the lateral half of the ball and socket type joint having a ball surface shaped such that a line tangent to the ball surface and at a location adjacent the central anterior-posterior axis lies substantially in an axial plane, the socket of the ball and socket type joint having a socket surface with a radius that closely matches a radius of curvature of the ball surface when the socket articulates about the ball.

44. The system of claim 43 further comprising:
a second anterior articulating assembly for implantation through a second approach, wherein the second approach is contralateral to the first approach.

45. A system for creating at least a portion of a coupling between a superior vertebra and an inferior vertebra comprising:
a first means for articulating in an intervertebral disc space between the superior and inferior vertebrae;
a second means for articulating in the intervertebral disc space;
a third means for articulating posteriorly of the intervertebral disc space;
a fourth means for articulating posteriorly of the intervertebral disc space;
a fifth means for coupling between the first means and the third means including at least a first bridge component having a length between the first means and the third means with two or more sides along the length;
a sixth means for coupling between the second means and the fourth means including at least a second bridge component having a length between the second means and the fourth means with two or more sides along the length;
an interlocking means for interlocking the first means and the second means,
wherein the first means is coupled to the second means by the interlocking means.

46. An artificial spinal joint for creating at least a portion of a coupling between a superior vertebra and an inferior vertebra comprising:
a first arthroplasty half comprising a first articulating joint replacement component for placement in an intervertebral disc space between the superior and inferior vertebrae, a first posterior joint replacement component spaced from the first articulating joint replacement component such that when the first articulating joint replacement component is configured to be disposed in the intervertebral disc space, the first posterior joint replacement component is configured to be disposed outside the intervertebral disc space and spaced apart from vertebral bodies of the superior vertebra and the inferior vertebra, and a first bridge component coupled between the first articulating joint replacement component and the first posterior joint replacement component, the first bridge component being an artificial pedicle configured to supplement or replace a first natural pedicle, wherein the artificial pedicle includes a length between the first articulating joint replacement component and the first posterior joint replacement component with two or more sides along the length; and
a second arthroplasty half comprising a second articulating joint replacement component for placement in an intervertebral disc space between the superior and inferior vertebrae, a second posterior joint replacement component spaced from the second articulating joint replacement component such that when the second articulating joint replacement component is configured to be disposed in the intervertebral disc space, the second posterior joint replacement component is configured to be disposed outside the intervertebral disc space and spaced apart from the vertebral bodies of the superior vertebra and the inferior vertebra, and a second bridge component coupled between the second articulating joint replacement component and the second posterior joint replacement component, the second bridge component being a second artificial pedicle configured to supplement or replace a second natural pedicle, wherein the second artificial pedicle includes a length between the second articulating joint replacement component and the second posterior joint replacement component with two or more sides along the length;
wherein the first articulating joint replacement abuts against the second articulating joint replacement component to form a unitary, substantially U-shaped implant.

* * * * *